(12) United States Patent
Tani

(10) Patent No.: US 7,168,878 B2
(45) Date of Patent: Jan. 30, 2007

(54) APPLICATOR CONTAINING A LIQUID FILLER

(75) Inventor: Yoshikazu Tani, Oji (JP)

(73) Assignee: Tokiwa Corporation, Nakatsugawa (JP)

( * ) Notice: Subject to any disclaimer, the term of this patent is extended or adjusted under 35 U.S.C. 154(b) by 191 days.

(21) Appl. No.: 10/914,144

(22) Filed: Aug. 10, 2004

(65) Prior Publication Data

US 2005/0063768 A1   Mar. 24, 2005

(30) Foreign Application Priority Data

Sep. 18, 2003   (JP) ............................. 2003-326695

(51) Int. Cl.
*A46B 11/04* (2006.01)
(52) U.S. Cl. ...................... 401/270; 401/268
(58) Field of Classification Search ........ 401/268–282, 401/286–288
See application file for complete search history.

(56) References Cited

U.S. PATENT DOCUMENTS 3,094,130 A * 6/1963 Wiener ....................... 401/190
4,279,527 A * 7/1981 Moe et al. .................. 401/277
4,726,386 A * 2/1988 Schultz ....................... 132/317
4,748,990 A * 6/1988 Brown et al. ............... 132/320
4,902,152 A * 2/1990 Seidler ........................ 401/117
5,222,824 A * 6/1993 Nicoll et al. ................ 401/235
5,345,644 A * 9/1994 Gueret ......................... 15/160
6,315,478 B1 * 11/2001 Atkins ......................... 401/37

* cited by examiner

*Primary Examiner*—Justine Yu
(74) *Attorney, Agent, or Firm*—Bacon & Thomas, PLLC

(57) ABSTRACT

To prevent leakage, excessive delivery and stagnation of a liquid material applied by an applicator, the applicator comprises a core member 2 having a hole part 2a, a projection part 2f and a communication hole 2j, an application member 3 made of an elastic material having a delivery hole 3f, and an inside space 4 between the front end side of the core member 2 and the application member 3, and structured such that the liquid material flows to the delivery hole 3f through a roundabout way via the hole part 2a, the communication hole 2j and the inside space 4 to cause fluid resistance and that the front face of the projection part 2f is close to or in contact with the delivery hole 3f to control delivery of the liquid material.

4 Claims, 18 Drawing Sheets

US 7,168,878 B2

APPLICATOR CONTAINING A LIQUID FILLER

BACKGROUND OF THE INVENTION

1. Field of the Invention

The present invention relates to an applicator for applying a liquid material filled therein.

2. Description of the Conventional Art

Conventionally, the following applicator (for example, referring to Japanese Patent Laid Open No. 2000-262324) is known as a liquid cosmetic extrudable container from which the liquid cosmetic is extruded for use. That is, the applicator comprises a main body cylinder having inside a filling region, in which the liquid cosmetic is filled, and an operating cylinder mounted in the state of being relatively rotatable at a rear end part of the main body cylinder. In this applicator, the application can be carried out, by a piston arranged in the filling region being advanced when the main body cylinder and the operating cylinder are relatively rotated, the liquid cosmetic being extruded to an front end side by advancing of the piston, and the extruded liquid cosmetic being delivered to an application body mounted on the front end of the main body cylinder, for example a brush or the like, through a pipe being a delivery route connected with the filling region.

SUMMARY OF THE INVENTION

In the liquid cosmetic extrudable container, there is a problem that a hand, clothing or the like may become dirty since the liquid cosmetic may leak from the front end of the container due to an impact, a vibration or the like by falling or the like of the container, or a viscosity change of the liquid cosmetic by a temperature change.

Furthermore, in the liquid cosmetic extrudable container, the liquid cosmetic is often delivered too much when applying the liquid cosmetic, so that it may be difficult to satisfactorily apply the liquid cosmetic.

The present invention was carried out in order to solve the above problems, and has an object to provide an applicator capable of preventing the occurring of dirt due to the leak of the liquid material filled therein, such as the liquid cosmetic, and satisfactorily applying the liquid material filled therein.

An applicator of the present invention comprises a core member, which is mounted on a front end part of a container body structured such that a liquid material filled in a filling region in the inside of the container body can be extruded toward a front end side, and has a hole part communicating with the filling region and extending to the front end side along the axis. The applicator also comprises an application member made of a soft elastic material and mounted to cover the front end side of said core member. An inside space is formed between the front end side of the core member and the application member of this applicator. The application member has a delivery hole communicating with a delivery port opened on a front end face of the application member and the inside space. The core member has a projection part and a communication hole. The projection part is provided at the front end side of the core member and projects toward the delivery hole of the application member so that an external face of the projection part is close to or in contact with the delivery hole. The communication hole is opened at the position except the front end of the projection part and communicates with the inside space and the hole part.

In such the applicator, a passage of the liquid material filled therein extends toward the delivery hole of the application member being closed to or contacted with the projection part, through the hole part, which is provided in the core member having the projection part at the front end side, communicates with the filling region and extends to the end side, the communication hole, which communicates with the hole part and opens at the position except the front end of the projection part, and the inside space, which is formed between the front end side of the core member and the application member. So, the liquid material filled therein does not flow to the delivery hole straightly at once, but flows to the delivery hole in a roundabout way so that the resistance may be given to the flow, and the outer face of the projection part is closed to or contacted with the delivery hole so that the delivery hole is narrowed or closed. Therefore, even when an impact or a vibration by falling or the like of the container, or a viscosity change or the like of the liquid material filled therein by a temperature change is worked, the leak of the liquid material filled therein can be prevented. In the case that the delivery hole is narrowed by the projection part being close to the delivery hole, it is possible to prevent the too much delivering of the liquid material filled therein in application, and thus the delivering amount becomes suitable. In the case that the delivery hole is closed by the projection part being in contact with the delivery hole, when the liquid material filled therein is extruded in the application, since the application member is constituted with a soft elastic material, an opening at the inside space side of the delivery hole of the application member is deformed so as to be displaced to the front end side, and stagnation of the liquid material filled therein in application can be prevented, and thus the delivering amount becomes suitable.

In this case, when the projection part is constituted to have a tapered conic-shape and the front end part of the projection part is inserted into the delivery hole, the above works are achieved most suitably.

Further, as the particular constitution for achieving the above works most effectively, the following constitution can be used. That is, the application member has a recessed part recessed in a rear end face of the application member, the front end side of the core member is inserted into the recessed part, and the inside space is formed between a bottom side of the recessed part and the front end side of the core member.

Furthermore, the application member has the following constitution. That is, the application member has a projection line on a plurality of places in a circumferential direction of a circumferential face of the recessed part. The projection line extends as much as a predetermined length from the bottom face side to the rear side of the recessed part and inwardly projects. The core member has a large diameter part and a groove part. The large diameter part is formed at the rear side from the projection part of the core member and fitted in the recessed part. The groove part extends as much as a predetermined length from the front end part to the rear side of the large diameter part and is fitted to the projection line. A second groove part is formed at the front end part of the groove part so as to be recessed at the further inside of the front end part and to reach the front end face of the large diameter part. The communication hole is opened at the second groove part by overlapping the inside face of the second groove part and an outer circumferential face of the hole part. When the application member has such the constitution, a rotation stopper of the application member can be constituted at the time of applying the liquid material filled therein, by the projection line of the application member and the groove part of the core member. Further, when the core member is molded by using an outer mold corresponding to an external shape of the core member and an inner mold corresponding to the hole part of the core member, the communication hole can be easily formed without an inner mold corresponding to the communication hole, by forming the part of the outer mold, which corresponds to the communication hole at the second groove part, to be in an outer mold-shape contacting with the inner mold.

Moreover, when a group of many projections having a brushing function is arranged around the delivery port of the application member, the skin dirt can be effectively removed by the projection group and a washing liquid, in the case that the liquid material filled therein is a washing liquid as the liquid cosmetic.

In addition, when the projection group is constituted to project in the direction inclined with respect to the axial direction of the application member, functions of the projection group can be diversified.

In this way, according to the applicator of the present invention, the occurrence of dirt to a hand or clothing or the like by leaking of the liquid material filled therein can be prevented beforehand, and the liquid material filled therein can be satisfactorily applied.

DETAILED DESCRIPTION OF PREFERRED EMBODIMENT

Hereinafter, the suitable preferred embodiment of the applicator of the present invention is explained with referring to FIG. 1 to FIG. 10.

Figure 1:
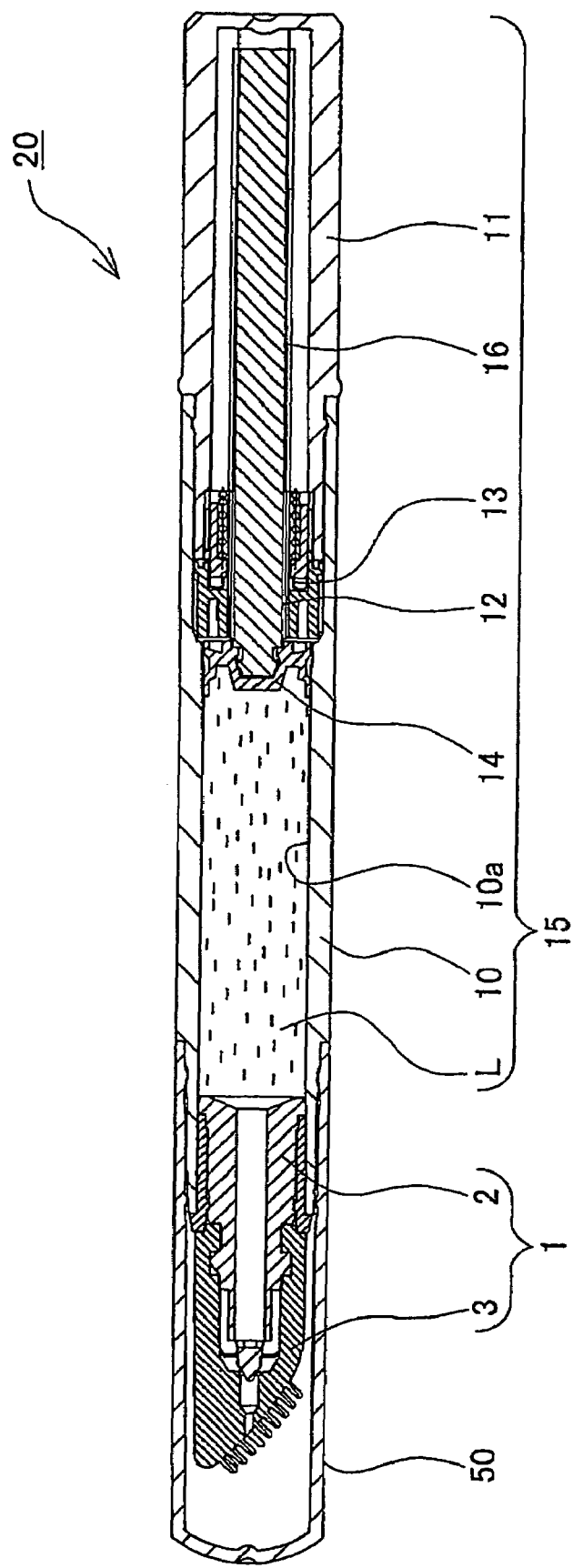
FIG. 1 is a longitudinal cross sectional view showing a liquid cosmetic extrudable container having an applicator according to an embodiment of the present invention.
Figure 2:
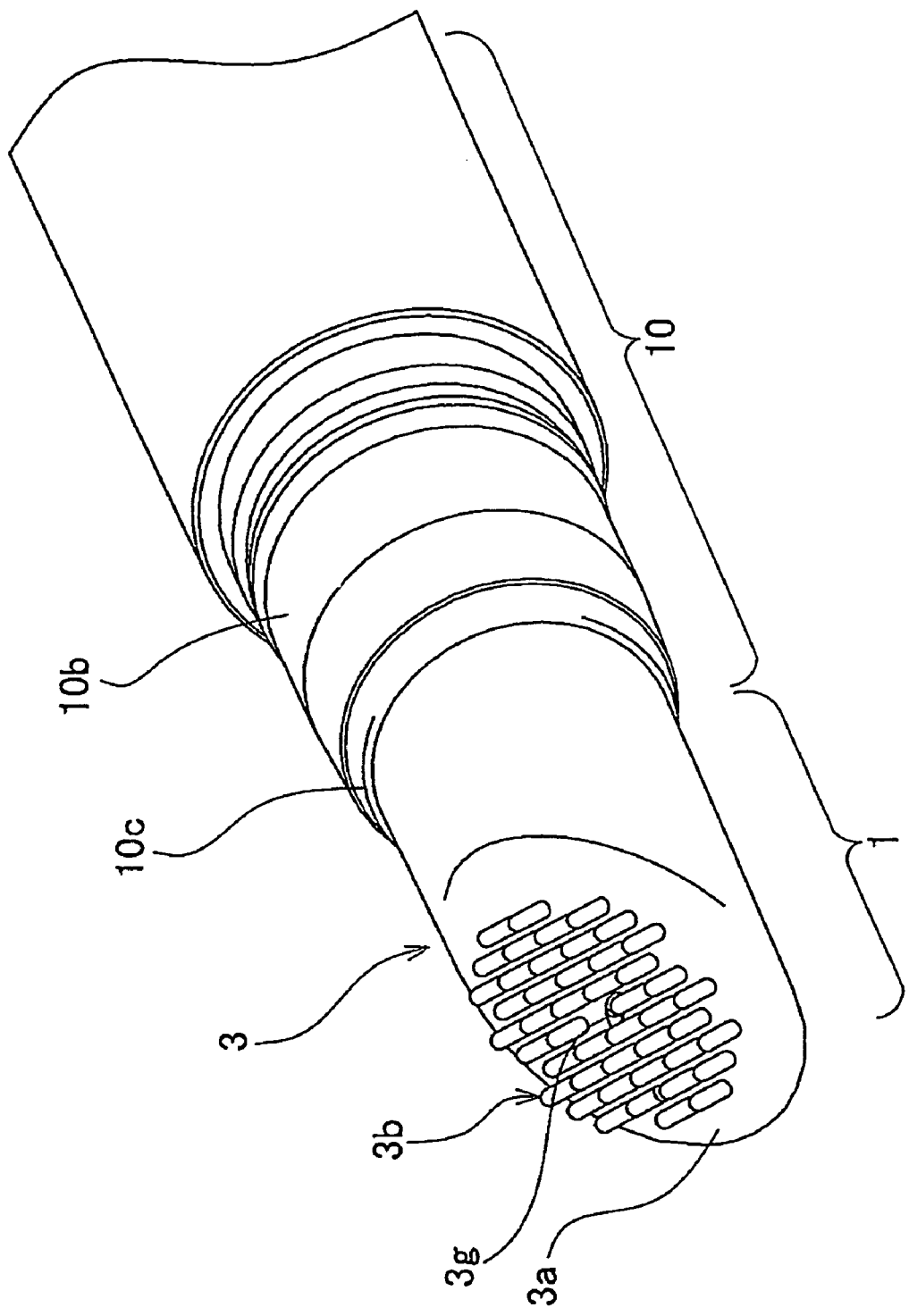
FIG. 2 is a perspective view of an front end part including an applicator of the liquid cosmetic extrudable container shown in FIG. 1.
Figure 3:
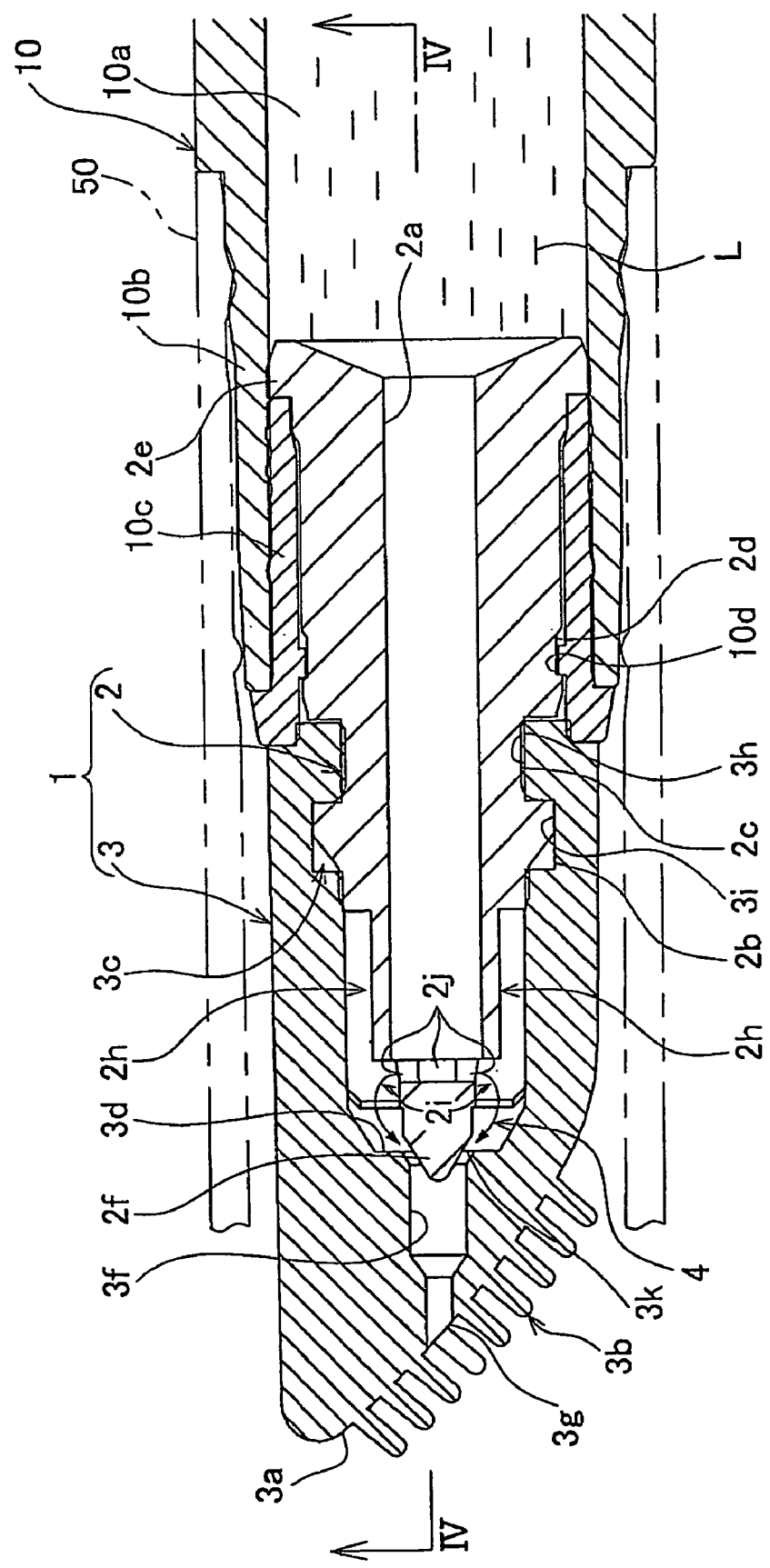
FIG. 3 is a longitudinal cross sectional view of FIG. 2.
Figure 4:
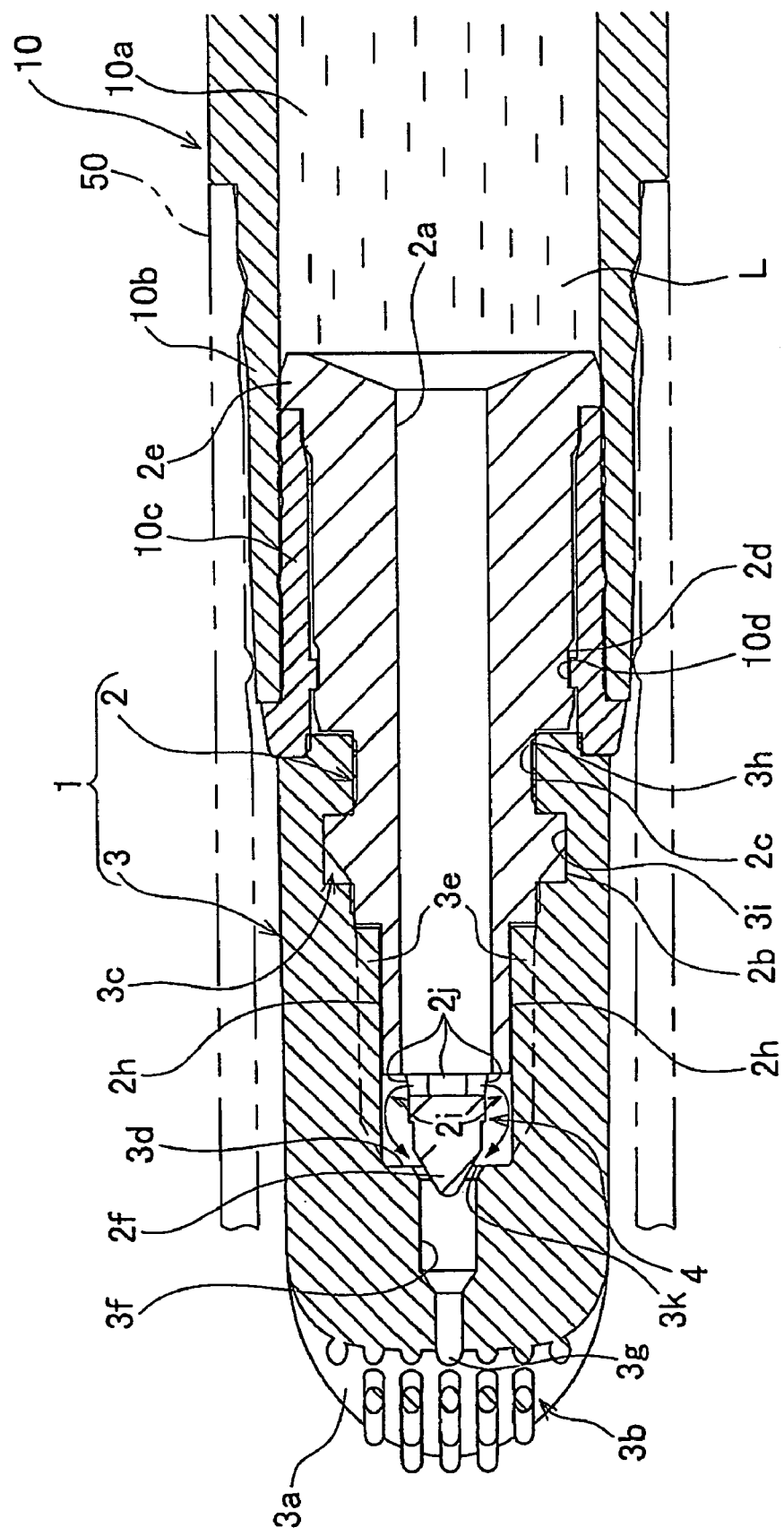
FIG. 4 is a cross sectional view at an arrow line IV—IV in FIG. 3.
Figure 5:
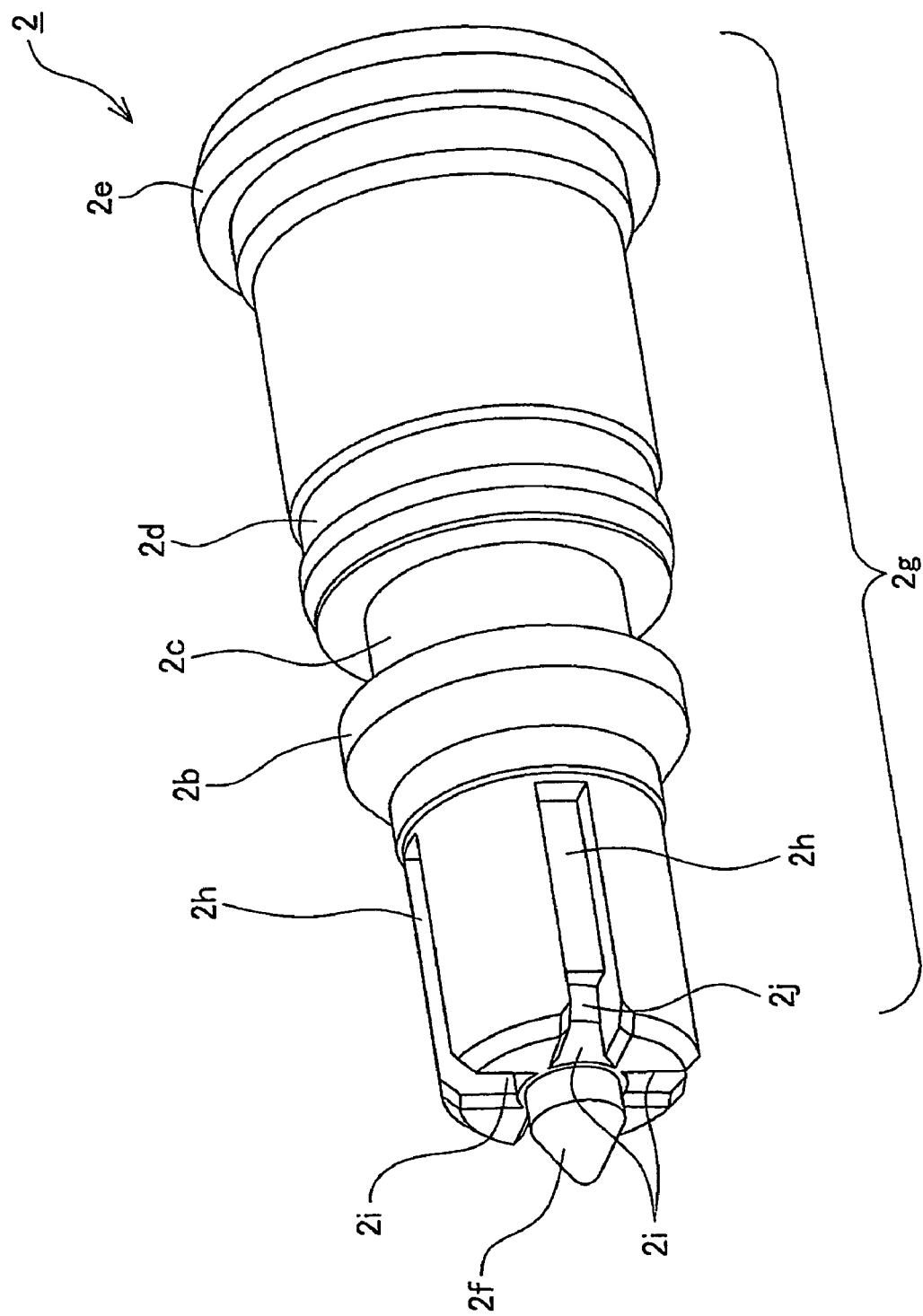
FIG. 5 is a perspective view showing a core member in FIG. 3 and FIG. 4.
Figure 6:
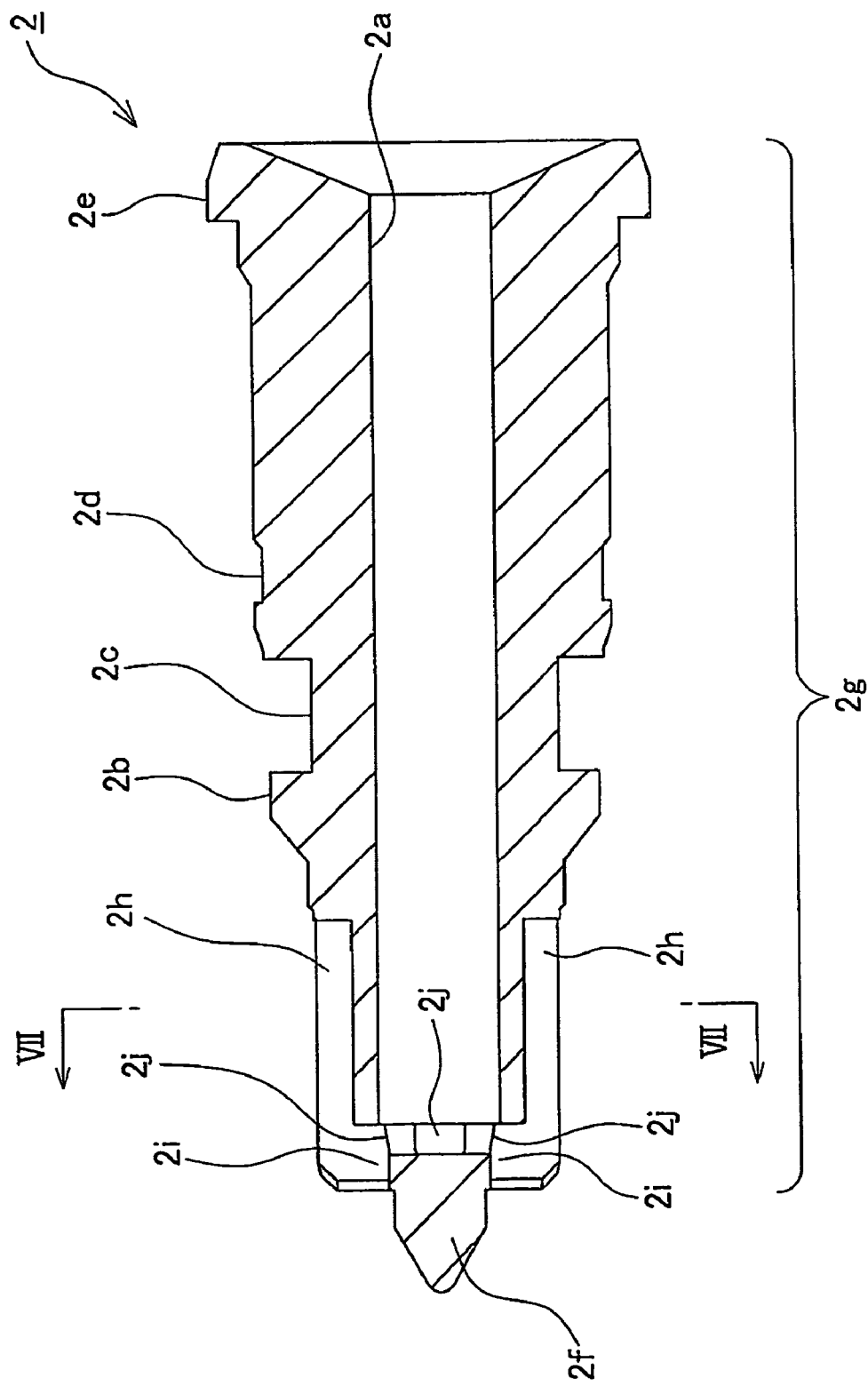
FIG. 6 is a longitudinal cross sectional view of a core member shown in FIG. 5.
Figure 7:
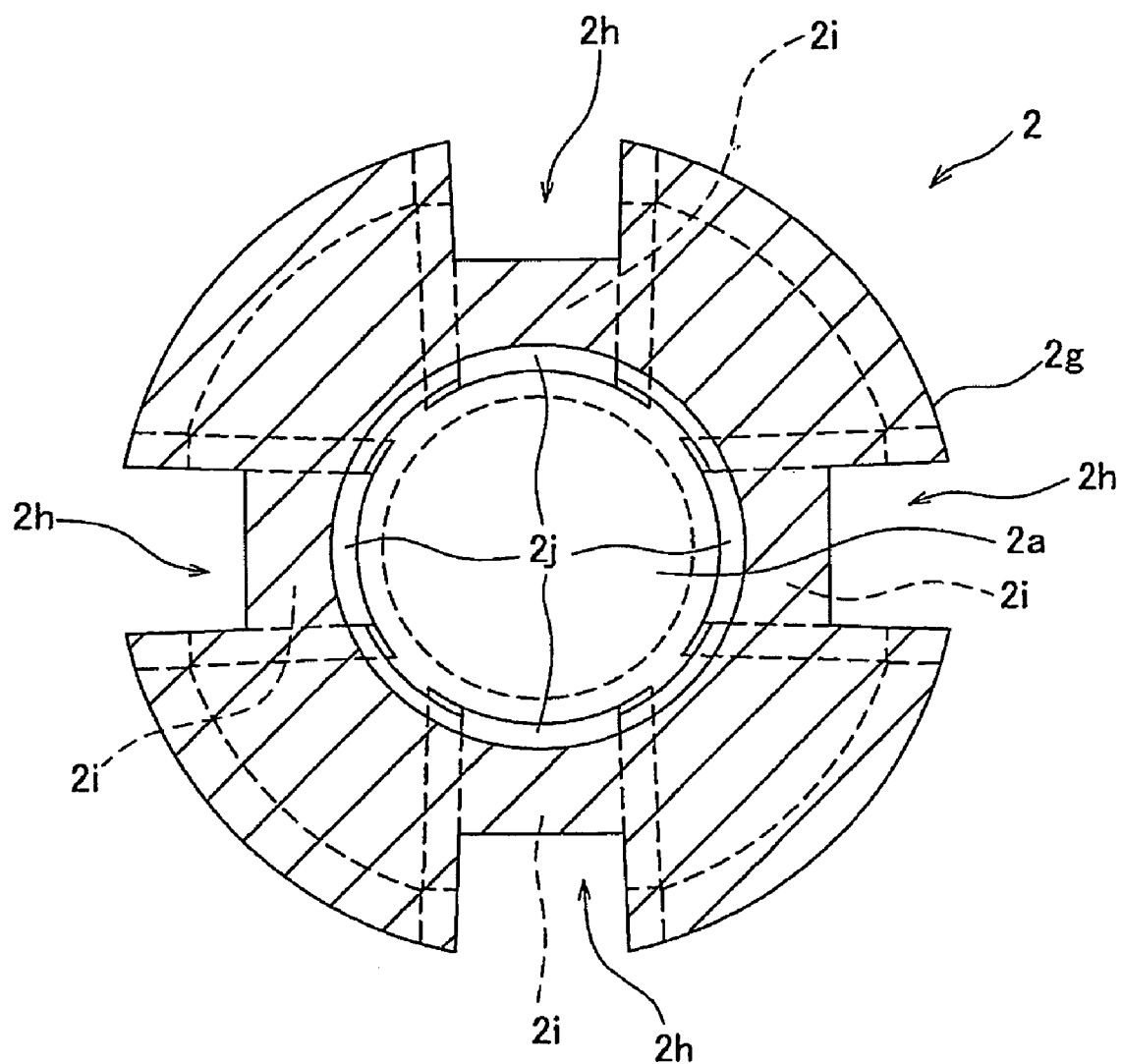
FIG. 7 is a cross sectional view at an arrow line VII—VII in FIG. 6.
Figure 8:
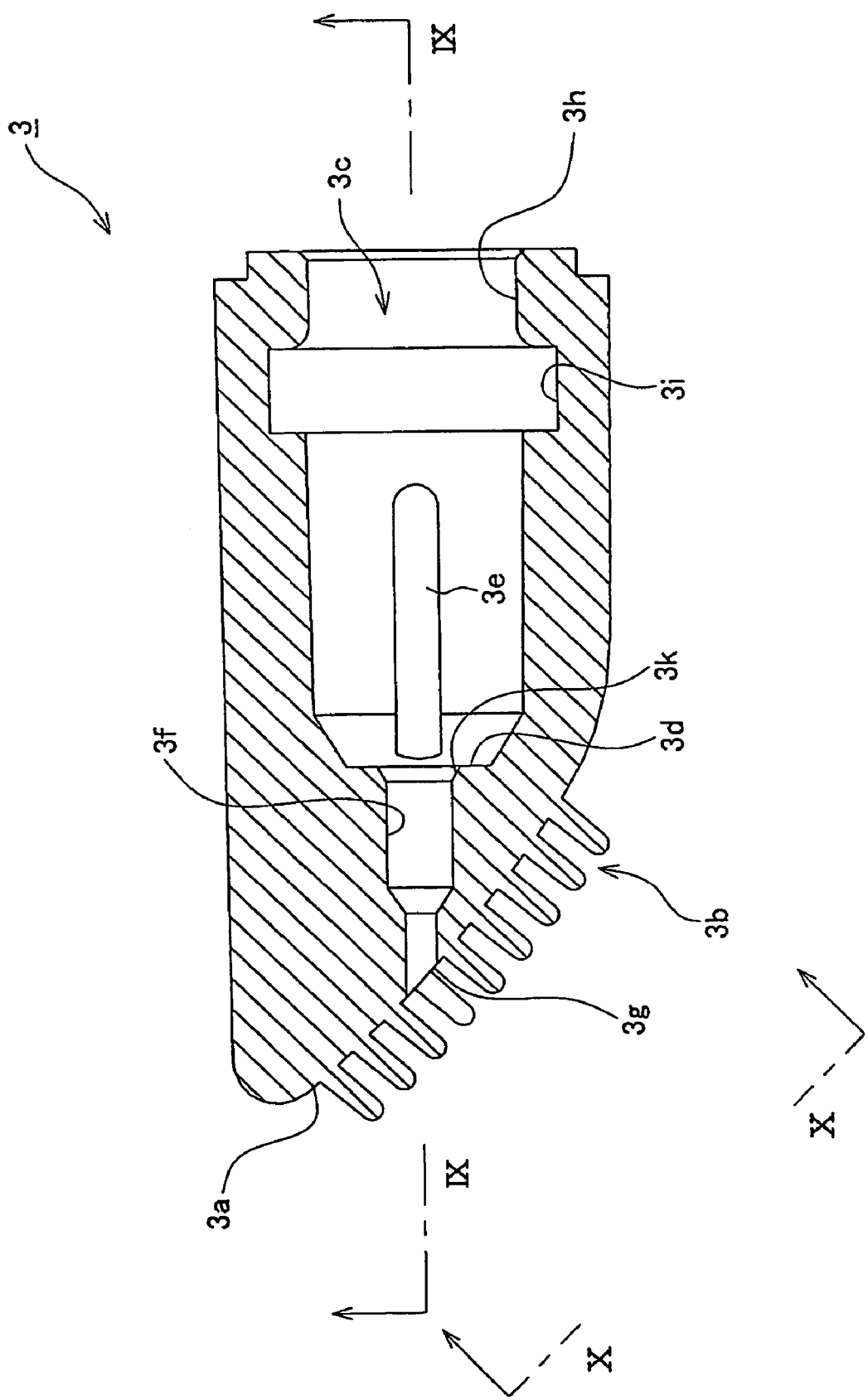
FIG. 8 is a longitudinal cross sectional view showing an application member in FIG. 3.
Figure 9:
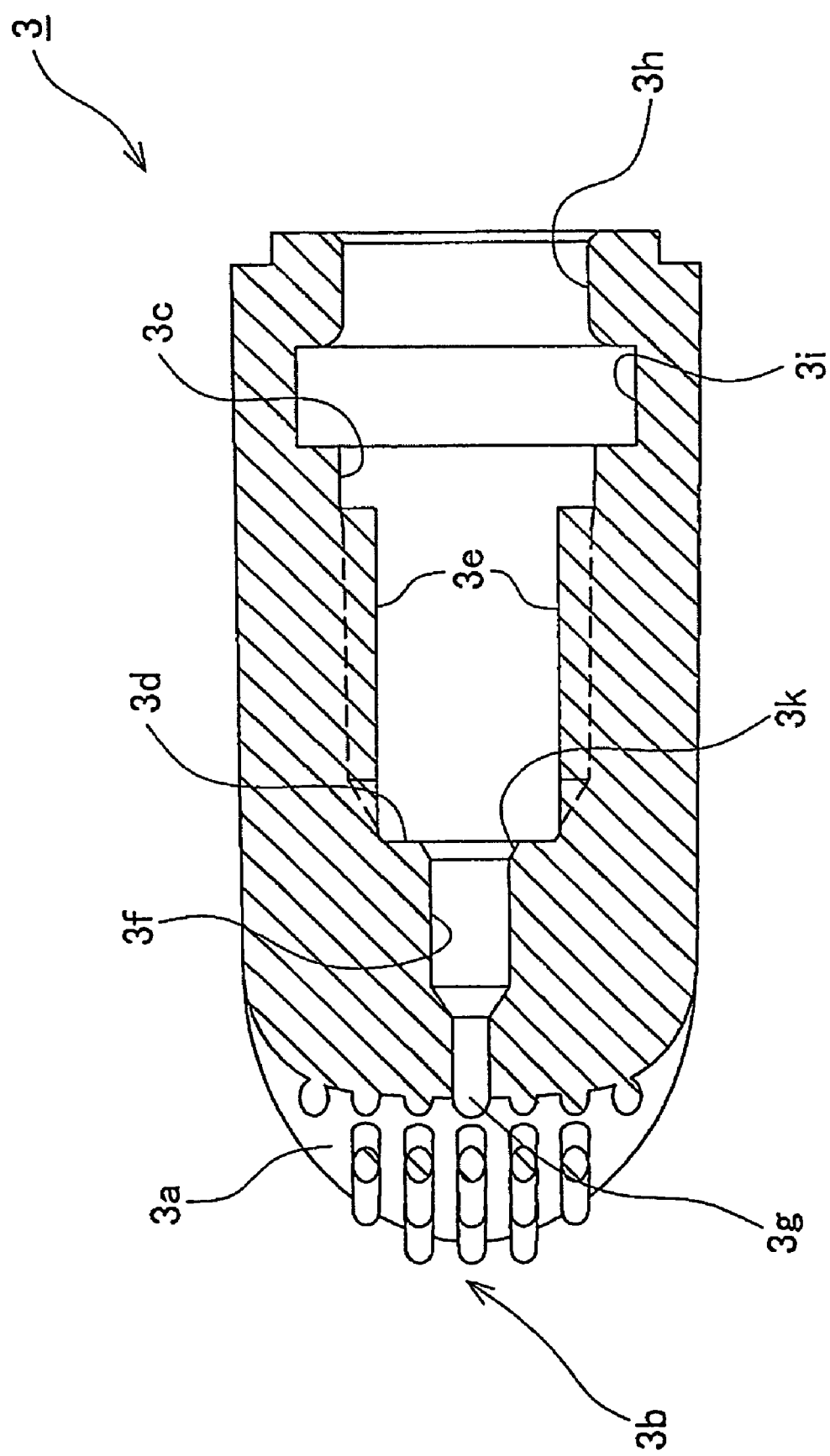
FIG. 9 is a sectional view at an arrow line IX—IX in FIG. 8.
Figure 10:
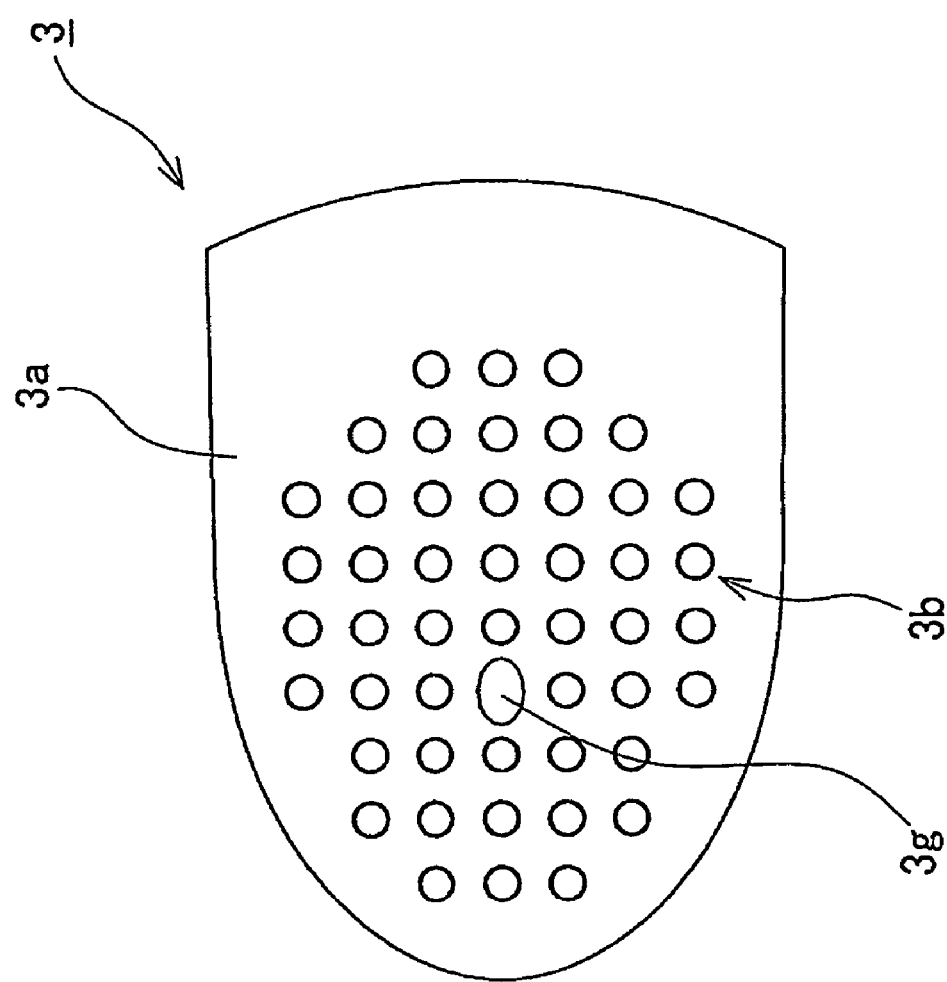
FIG. 10 is a cross sectional view at an arrow line X—X in FIG. 8.

FIG. 1 to FIG. 10 are each figure showing the applicator according to the embodiment of the present invention. FIG. 1 is a longitudinal cross sectional view showing the liquid cosmetic extrudable container having an applicator according to an embodiment of the present invention. FIG. 2 is a perspective view of the end part including the applicator of the liquid cosmetic extrudable container. FIG. 3 and FIG. 4 are longitudinal cross sectional views where the cross sectional positions are 90° different respectively from the position of FIG. 2. FIG. 5 to FIG. 7 are each view particularly showing the core member constituting the applicator. FIG. 8 to FIG. 10 are views particularly showing the application member constituting the applicator. The applicator of the embodiment of the present invention is applied to the liquid cosmetic extrudable container.

As shown in FIG. 1, a liquid cosmetic extrudable container 20 has the same constitution as that described in Japanese Patent Laid Open No. 2000-262324, except an applicator 1 constituting a front end part of the container 20. More particularly, the container 20 has the following constitution as a container body 15. In the container body 15, when a main body cylinder 10 and an operating cylinder 11 are relatively rotated by a user, a piston 14 arranged in a filling region 10a is advanced gradually toward the front end of the main body cylinder 10, and a liquid cosmetic L in the filling region 10a is extruded gradually toward the front end. The main body cylinder 10 has the filling region 10a at the inside, in which the liquid cosmetic L is filled. The operating cylinder 11 is mounted in the state of being relatively rotatable at a rear end part of the main body cylinder 10. The piston 14 is advanced according to a screw mechanism 12, a rotation stopping mechanism 16, and a ratchet mechanism 13, which are extruding mechanisms constituted in the container 20. The ratchet mechanism allows the piston 14 to rotate only in one direction.

In the embodiment of the present invention, a washing liquid such as a cleansing oil or the like is filled in the filling region 10a of the container body 15. Then, the applicator 1 mounted on the front end part of the container body 15 is for applying the washing liquid extruded from the filling region 10a by the piston 14 to a skin for effectively removing the dirt or the like of a skin.

The main body cylinder 10 constituting the container body 15 has a cylindrical applicator holding member 10c, which is fitted in a front end cylinder part 10b and mounted, as shown in FIG. 2 to FIG. 4. In the applicator holding member 10c, an annular projection part 10d for mounting a core member 2 is formed on an inner peripheral face of a front end side of the applicator holding member 10c, as shown in FIG. 3 and FIG. 4.

The applicator 1 has the core member 2 and an application member 3. The core member 2 is mounted on the main body cylinder 10, for introducing the washing liquid from the filling region 10a to the front end side and controlling the flow of the washing liquid. The application member 3 is mounted so as to cover the end side of the core member 2, for applying the washing liquid from the core member 2.

The core member 2 is made with, for example, polyethylene, polypropylene or other plastic materials. The core member 2 is formed in a stepped approximately cylindrical-shape comprising an annular projection part and groove part at its outer periphery, as shown in FIG. 3 to FIG. 7. Further, the core member 2 has a hole part 2a extending from the rear end face to the front end side along with the axis, as shown in FIGS. 3, 4 and 6.

On the outer peripheral face of the core member 2, as shown in FIG. 3 to FIG. 6, an annular projection part 2b and an annular groove part 2c is formed at a position of the middle in an axial direction for mounting an application member 3. Further, an annular groove part 2d is formed at a position of a rear side of the annular projection part 2b and the annular groove part 2c. An annular projection part 10d of the applicator holding body 10c is fitted in the annular groove part 2d. Furthermore, an annular collar part 2e is formed at a rear end position. The annular collar part 2e outwardly projects and contacted with a rear end face of the applicator holding body 10c.

Furthermore, as shown in FIG. 5 and FIG. 6, the core member 2 has a projection part 2f projecting frontward at the front end part thereof, and the rear side from the projection part 2f is a large diameter part 2g having the larger diameter than that of the projection part 2f. The projection part 2f is for controlling the flow of the washing liquid, and has a tapered conic-shape.

The outer periphery of the large diameter part 2g of the core member 2 has a groove part 2h, which extends as much as predetermined length from the front end to the rear side of the large diameter part 2g and reaches near the annular projection part 2b. The groove parts 2h, which work as the rotation stopper of the application member 3, are respectively provided at positions separated by 90° in the peripheral direction of the large diameter part 2g, as shown in FIG. 5 and FIG. 7.

Furthermore, as shown in FIG. 5 and FIG. 6, a second groove part 2i is formed at the front end part of the groove part 2h of the large diameter part 2g of the core member 2, and the second groove part 2i is recessed further inside and reaches the front end face of the large diameter part 2g. An inside face of the second groove part 2i is overlapped with the outer peripheral face of the hole part 2a, as shown in FIG. 6, and a communication hole 2j is opened at the overlapping position, as shown in FIG. 5 to FIG. 7. The communication hole 2j communicates with the hole part 2a and the outside of the core member 2 (in other words, extends from the front end of the hole part 2a to the outside in a radius direction to communicate with the outside of the core member 2).

The core member 2 having such the constitution can be manufactured by the following manufacturing method. That is, the method comprises, using the outer mold corresponding to the external shape of the core member 2 and the inner mold corresponding to the hole part 2a of the core member 2, making the part corresponding to the communication hole 2j of the second groove part 2i of the outer mold to be in the outer mold-shape contacting with the inner mold, pouring a predetermined resin into the outer mold, and solidifying and demolding it. Therefore, the communication hole 2j can be easily formed without the inner mold corresponding to the communication hole 2j, and thus the manufacturing cost can be reduced.

The application member 3 is molded with the soft elastic material, such as a silicone rubber or the like. The application member 3 is constituted to have an approximately cylindrical-shape, and a front end face 3a of the application member 3 has an inclined face being suitable for application, as shown in FIG. 2 to FIG. 4, FIG. 8 and FIG. 9. On the inclined front end face 3a, a group of many projections having a brushing function is provided by integral molding.

The application member 8 has a recessed part 3c recessed from the rear end face, as shown in FIGS. 3, 4, 8 and 9. The recessed part 3c has the shape corresponding to a round external shape of the part from the front end of the large diameter part 2g to the annular groove part 2c, as shown in FIG. 4. Thereby, the part from the front end of the large diameter part 2g to the annular groove part 2c can be fitted in this recessed part 3c (refer to FIG. 5 and FIG. 6). The recessed part 3c also has an annular projection part 3h at the position of the rear end part, and an annular groove part 3i at the position adjacent to the front side of the annular projection part 3h. The annular projection part 3h is fitted in the annular groove part 2c of the core member 2, and the annular groove part 3i is fitted in the annular projection part 2b of the core member 2.

Furthermore, the application member 3 has the constitution, in which the part corresponding to the external shape of the front end of the large diameter part 2g extends further to the front end side and a bottom face 3d of the recessed part 3c is formed.

On the peripheral face of the front end side of the recessed part 3c, a projection line 3e is formed, as shown in FIGS. 4, 8 and 9. The projection line 3e extends as much as predetermined length from the bottom face 3d side to the rear side of the recessed part 3c, inwardly projects, and enters into and fits in two of four groove parts 2h of the core member 2. The projection line is formed at positions separated by 180° in the peripheral direction of the recessed part 3c.

Moreover, the application member 3 has a delivery hole 3f. The delivery hole 3f has a smaller diameter than that of the bottom face 3d of the recessed part 3c and communicates with the bottom face 3d and the front end face 3a. The delivery hole 3f is constituted to have a circular cross section. An opening on the front end face 3a of the delivery hole 3f is a delivery port 3g, and a group of many projections 3b are provided around the delivery port 3g, as shown in FIG. 8 to FIG. 10.

In addition, the application member 3 can be made of one suitably selected from a variety of materials, such as LDPE, thermoplastic elastomer or the like, by the injection molding method, in addition to silicone rubber, ethylene propylene rubber, isopropylene rubber or the like, by the compression molding method. For example, an application member made by laminating a nylon net and a foamed porous polyurethane sheet and cutting out it can be mounted, and a brush, a hair comb or the like comprising polyester fibers can be also mounted.

Furthermore, the application member 3, the core member 2 and the applicator holding body 10c are assembled as an assembly unit, and are mounted on the main body cylinder 10 after filling the washing liquid in the filling region 10a.

That is, as shown in FIG. 3 and FIG. 4, the core member 2 is mounted on the applicator holding member 10c, by inserting the front end side of the core member 2 from the opening at the rear end of the applicator holding member 10c, butting the annular collar part 2e against the rear end face of the applicator holding member 10c, and engaging the annular projection part 10d of the applicator holding member 10c with the annular groove part 2d. The application member 3 is mounted on the core member 2, by externally putting the rear end side of the application member 3 so as to cover the front end side of the core member 2, butting the rear end face of the application member 3 against the front end face of the applicator holding body 10c, respectively engaging the annular projection part 3h with the annular groove part 2c of the core member 2, the annular groove part 3i with the annular projection part 2b of the core member 2, and the two projection lines 3e with the groove parts 2h of the core member 2 so as to constitute the rotation stopper. Thereby, the assembly unit having the application member 3, the core member 2 and the applicator holding member 10c is constituted, and the applicator holding body member 10c constituting the assembly unit is fitted in the front end cylindrical part 10b of the main body cylinder 10. Then, the assembly unit is mounted on the main body cylinder 10 where the annular collar part 2e of the core member 2 is airtightly bonded to the inner peripheral face of the main body cylinder 10.

In this state, the hole part 2a of the core member 2 communicates with the filling region 10a.

Moreover, in this state, a predetermined inside space 4 is formed between the bottom face 3d side of the recessed part 3c of the application member 3 and the front end part of the core member 2, more particularly, between the bottom face 3d side of the recessed part 3c of the application member 3, and the projection part 2f and the second groove part 2i of the core member 2. With this inside space 4, the communication hole 2j opening at the second groove part 2i of the core member 2 communicates, and an opening 3k at the recessed part 3c side (the inside space 4 side) of the delivery hole 3f of the application member 3 communicates.

Furthermore, in this state, the projection part 2f of the core member 2 projects toward the delivery hole 3f of the application 3, the front end part of the projection part 2f enters into the delivery hole 3f, and the outer face of the front end part is positioned close to the delivery hole 3f with keeping a predetermined space.

Moreover, the applicator 1 having the core member 2 and the application member 3 is covered and protected by a cap 50 which is detachably mounted on the front end cylindrical part 10b of the main body cylinder 10, as shown in FIG. 1.

Next, the case when the washing liquid is applied using a liquid cosmetic extrudable container 20 having such the applicator 1 is explained with reference to FIG. 3 and FIG. 4. When the washing liquid is extruded from the filling region 10a by an operation of a user, a passage of the washing liquid extends toward the delivery hole 3f of the application member 3 through the hole part 2a and the communication hole 2j of the core member 2 and the inside space 4. So, the washing liquid does not flow toward the delivery hole 3f straightly at once, but flows in a roundabout way so that the resistance may be given to the flow, as shown with an arrow in the figure. In addition, the outer face of the projection part 2f of the core member 2 has a constitution being close to the delivery hole 3f, so that the delivery hole 3f is narrowed or closed.

Therefore, it can be prevented to deliver too much the washing liquid in application so that the delivering amount becomes suitable, and thus the washing liquid is satisfactory applied.

At this time, since a group of many projections 3b having a brushing function is arranged around the delivery port 3g of the application member 3, the dirt of skin, especially, the dirt of pores can be effectively removed by a group of these projections 3b and the washing liquid. Furthermore, since a group of the projections 3b projects in the direction inclined with respect to the axial direction of the application member 3 (a group of the projections 3b are vertically provided with respect to the inclined end face 3a), the dirt can be removed much more effectively.

Furthermore, at this time, since the rotation stopper of the application member 3 is constituted by the projection line 3e of the application member 3 and the groove part 2h of the core member 2, the application member 3 is not rotated at the time of applying, so that the washing liquid can be applied much more satisfactory.

Furthermore, even when an impact or a vibration by falling or the like, or a viscosity change or the like of the washing liquid by a temperature change is worked to the liquid cosmetic extrudable container 20 having such the applicator 1, the leak of the washing liquid can be prevented since the delivery hole 3f is narrowed and the passage of the washing liquid is made roundabout. Therefore, it can be prevented beforehand that a hand, clothing or the like becomes dirty.

In addition, the space between the outer face of the projection part 2f of the core member 2 and the delivery hole 3f can be controlled depending on, for example, viscosity of the washing liquid or the like.

Furthermore, in the present embodiment, the communication hole 2j is provided to extend from the hole part 2a of the core member 2 to the outside in a radius direction, in order to flow the washing liquid in a roundabout way from the communication hole 2j of the core member 2 to the delivery hole 3f. In this case, the communication hole 2j may be an inclined hole or the like. That is, it can be used if the communication hole 2j opens at the position except the end of the projection part 2f of the core member 2, faces to the inside space 4, and communicates with the hole part 2a.

Figure 11:
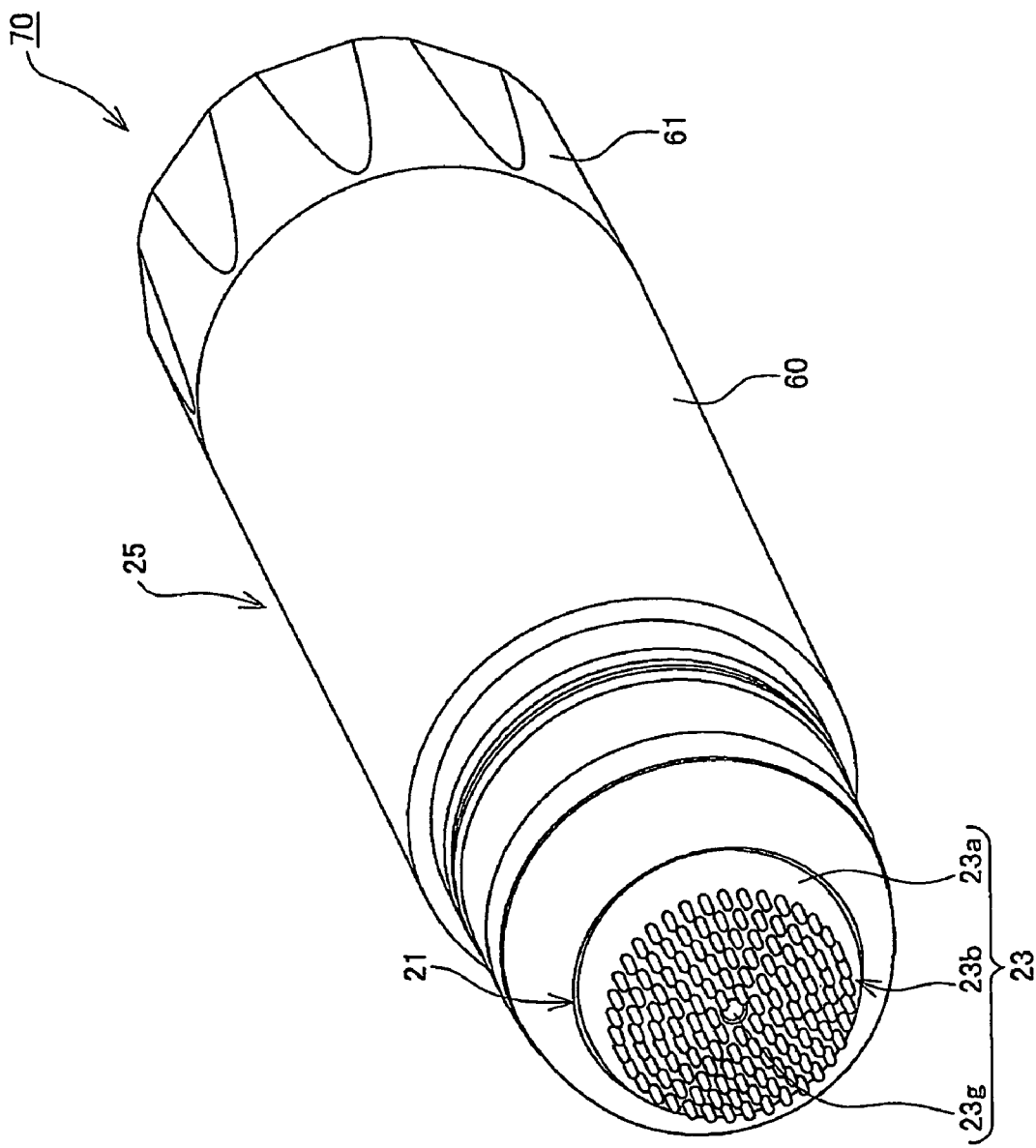
FIG. 11 is a perspective view showing a liquid cosmetic extrudable container having an applicator according to another embodiment of the present invention.
Figure 12:
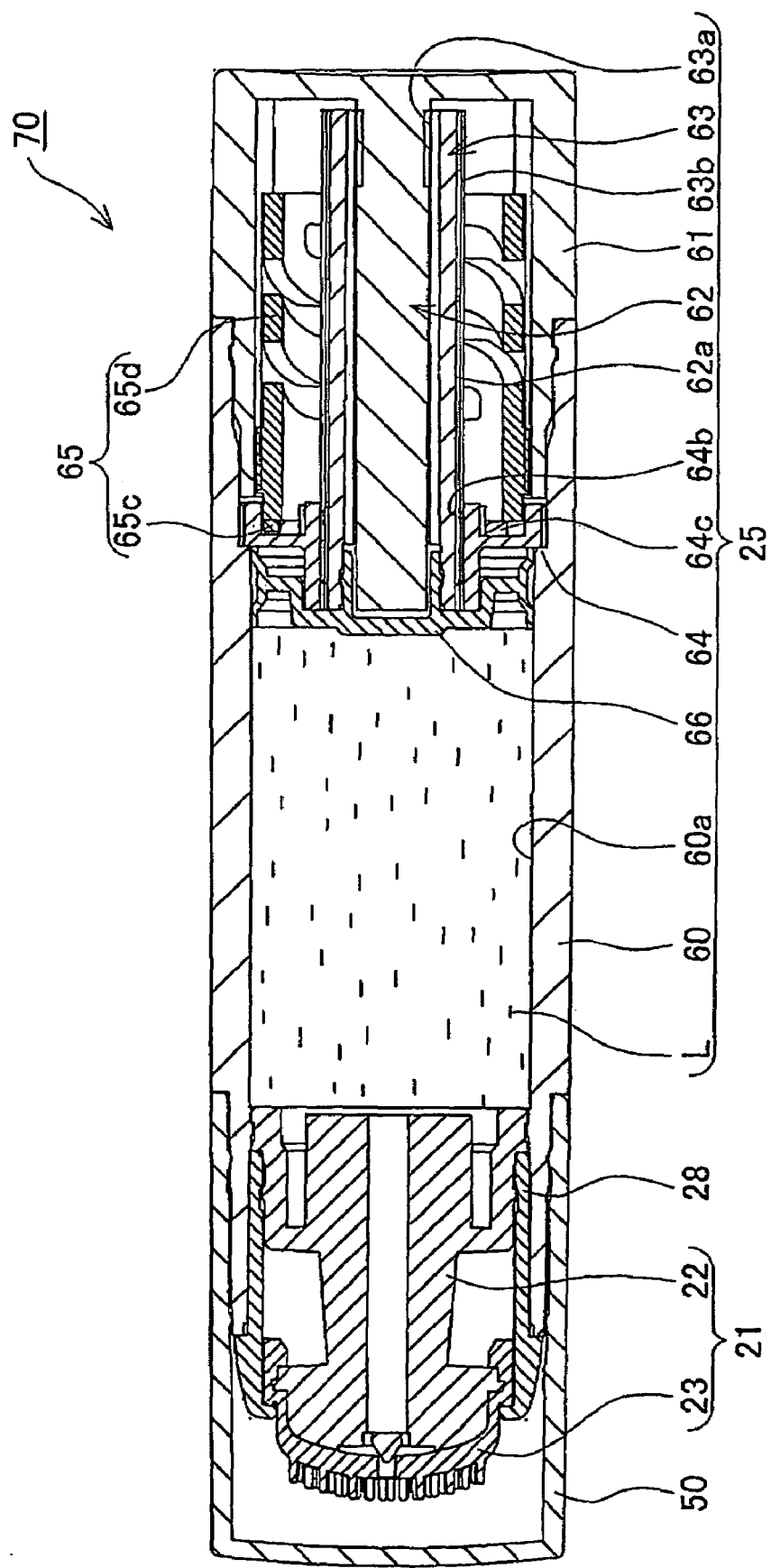
FIG. 12 is a longitudinal cross sectional view of the liquid cosmetic extrudable container shown in FIG. 11.
Figure 13:
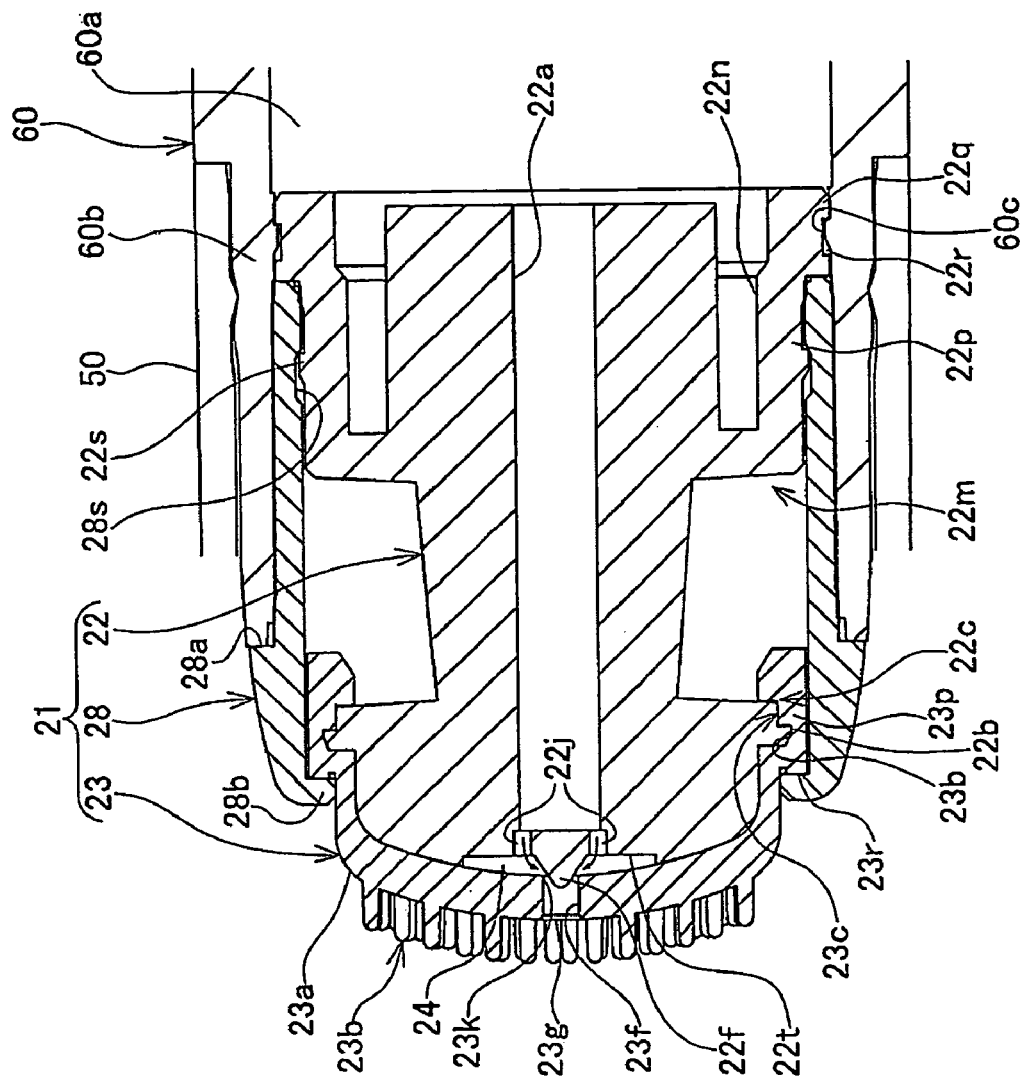
FIG. 13 is a longitudinal cross sectional view of a front end part including the applicator of the liquid cosmetic extrudable container shown in FIG. 12.
Figure 14:
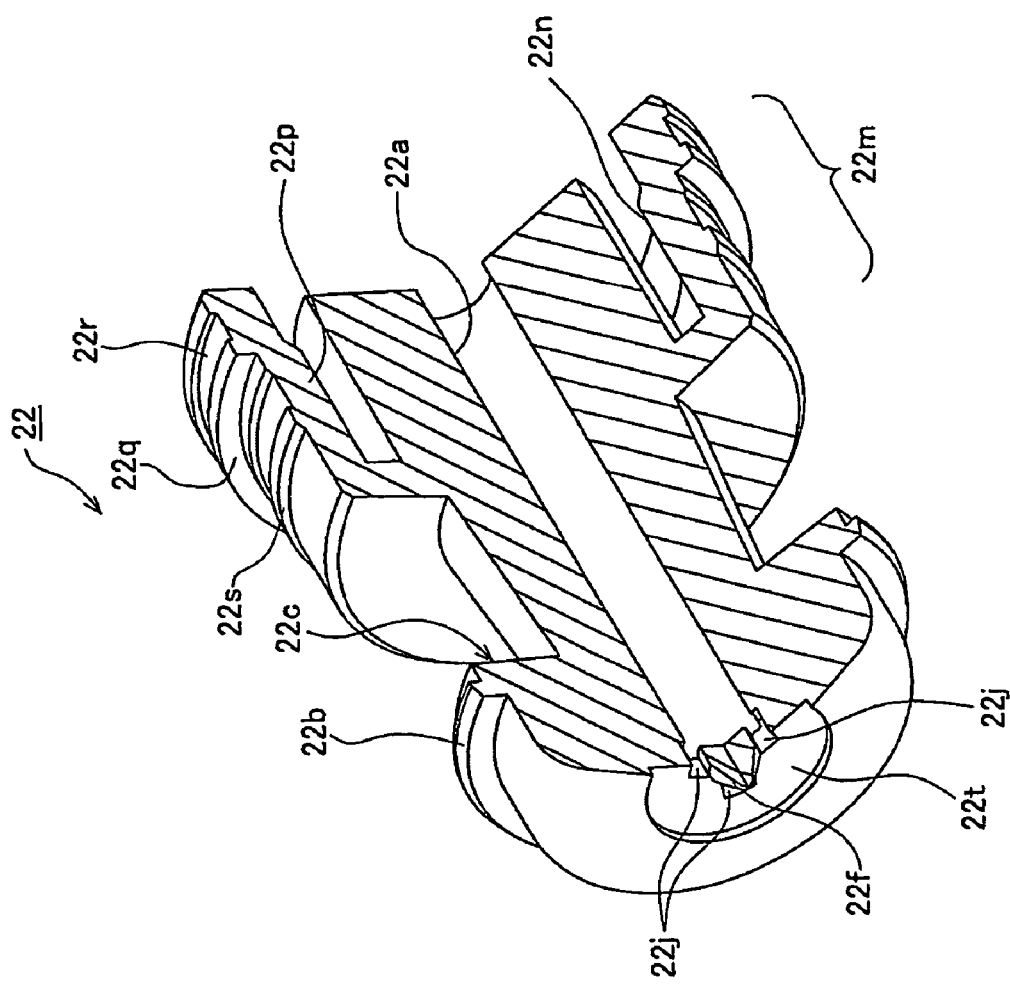
FIG. 14 is a broken perspective view showing a core member in FIG. 13.
Figure 15:
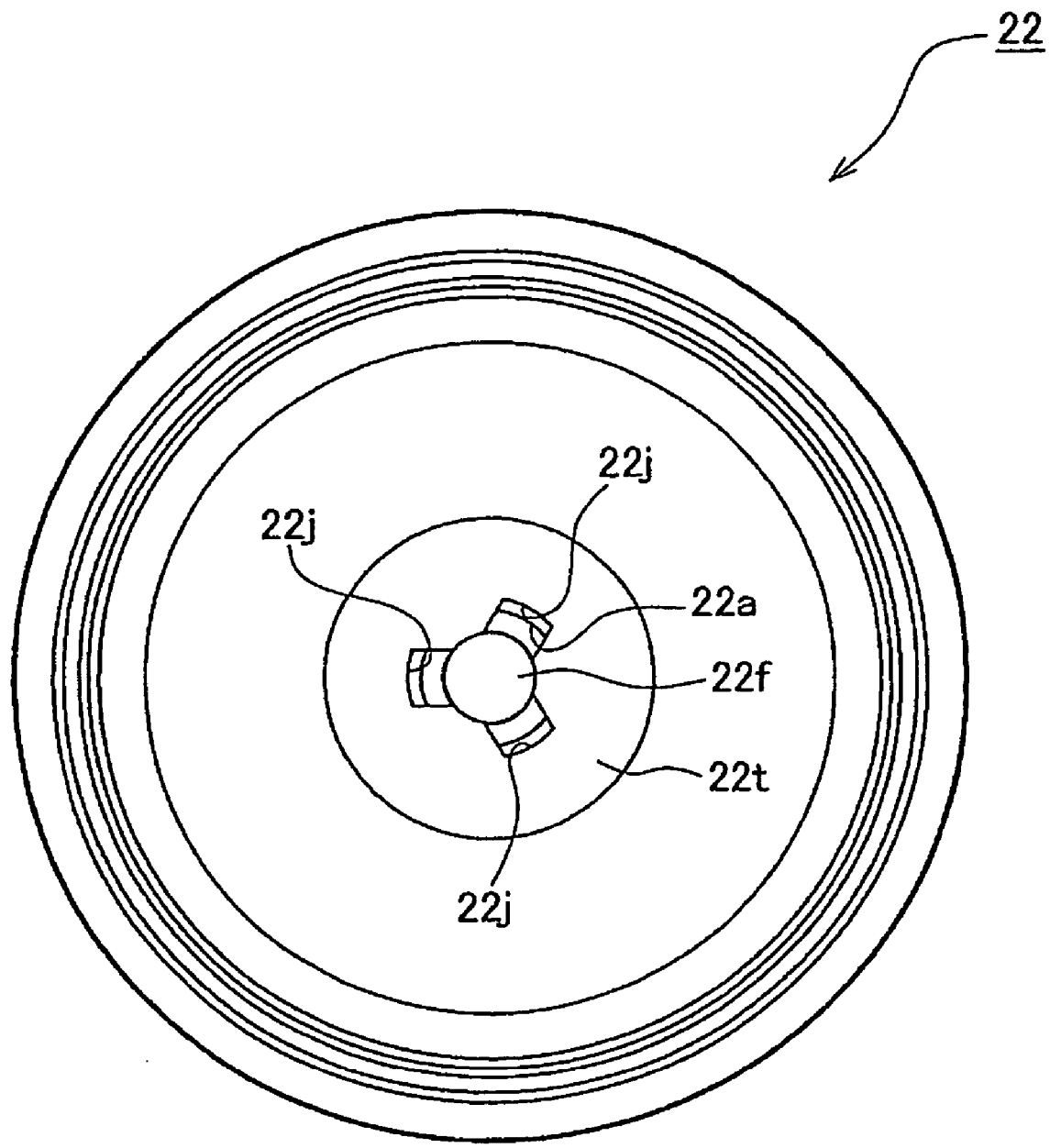
FIG. 15 is a front view of a core member shown in FIG. 14.

FIG. 11 to FIG. 15 each show the applicator according to another embodiment of the present invention. FIG. 11 and FIG. 12 each show the liquid cosmetic extrudable container having the applicator according to another embodiment of the present invention. FIG. 13 is a longitudinal cross sectional view of the front end part including the applicator of the liquid cosmetic extrudable container. FIG. 14 and FIG. 15 each particularly show the core member constituting the applicator. In addition, in following figures, when factors are the same as or equivalent to those in the above figures, same codes are applied to omit the repeated explanations.

The point that an applicator 21 of the embodiment differs from the applicator of the foregoing embodiment is that, as shown in FIG. 13, a recessed part 22t is provided at a core member 22 to form a predetermined inside space 24 between a front end side of the core member 22 and an application member 23 and, in connection with this, shapes of the core member 22 and the application member 23 are changed to be different from the core member 2 and the application member 3 of the foregoing embodiment.

Hereinafter, before explaining the applicator 21 having the core member 22 and the application member 23, a constitution of the a container body 25 except the applicator 21 of a liquid cosmetic extrudable container 70 is explained at first, referring with FIG. 11 and FIG. 12.

The container body 25 is constituted to have a cylindrical main body cylinder 60, a bottomed operating cylinder 61, a cylindrical shaft body 62, a cylindrical moving body 63, a cylindrical cylinder body 64 having a collar, and a cylindrical ratchet spring part 65. The cylindrical main body 60 has inside a filling region 60a, in-which the liquid cosmetic L is filled, as shown in FIG. 12. The bottomed operating cylinder 61 is relatively rotatably provided at a rear end of the main body 60, as shown in FIG. 11 and FIG. 12. The cylindrical shaft body 62 is set upright at a bottomed part of the operating cylinder 61 and a rotation stopper 62a extending in the axial direction is formed on an outer peripheral face of this shaft body 62, as shown in FIG. 12. The cylindrical moving body 63 is externally mounted on the shaft body 62. A rotation stopper 63a engaging with the rotation stopper 62a of the shaft body 62 is formed on an inner peripheral face of the cylindrical moving body 63, and a male screw 63b is formed on an outer peripheral face of the cylindrical moving body 63. The cylindrical cylinder body 64 having a collar is connected with the main body cylinder 60, and a female screw 64b screwing with a male screw 63b of the moving body 63 is formed on an inner peripheral face of the cylindrical cylinder body 64. The cylindrical cylinder body 64 also has a ratchet teeth 64c on the rear end face thereof. The ratchet spring part 65 is arranged between the cylindrical body 64 and the operating cylinder 61 and has a ratchet teeth 65c gearing with the ratchet teeth 64c of the cylindrical body 64 on the front end face thereof. A compression spring part 65d is made at the rear side from the ratchet teeth 65c and unrotatably engaged with the side of the operating cylinder 61. When a user relatively rotates the main body cylinder 60 and the operating cylinder 61, the moving body 63 is straightly moved to the front end side, according to a screwing mechanism, a rotation stopping mechanism and a ratchet mechanism. The screwing mechanism comprises the male screw 63b of the moving body 63 and the female screw 64b of the cylindrical body 64. The rotation stopping mechanism comprises the rotation stopper 62a of the shaft body 62 and the rotation stopper 63a of the moving body 63. The ratchet mechanism comprises the ratchet teeth 64c of the cylindrical body 64 and the ratchet spring part 65, and allows the rotation in one direction. In accordance with this straightly moving, a piston 66 provided at the front end of the moving body 63 slides the filling region 60a and extrudes gradually the washing liquid in the filling region 60a.

Next, the core member 22 and the application member 23 are particularly explained. The core member 22 and the application member 23 are constituted with the same molding materials as those of the foregoin embodiment.

The core member 22 has an stepped approximately cylindrical-shape comprising the annular projection and groove parts at the outer periphery, as shown in FIG. 13 to FIG. 15, and has a hole part 22a extending from the rear end face to the front end side along the axis, as shown in FIG. 13 and FIG. 14.

On the outer peripheral face of the core member 22, an annular projection part 22b and a stepped annular groove part 22c for mounting the application member 23 are formed at the position close to the front end side, and a part from the rear end position of the annular groove part 22c to the rear end face of the core member 22 is a large diameter part 22m. The core member 22 has an annular groove part 22n and an annular projection part 22p. The annular groove part 22n is provided at a position surrounding the hole part 22a of the rear end face of the core member 22, and recessed from the rear end face to near the front end of the large diameter 22m. The annular projection part 22p is rearwardly projected at an outer peripheral position of the large diameter part 22m by forming the annular grove part 22n. Since the annular projection part 22p is separated from the hole part 22a side (a part of an axis center side) of the core member 22 by the annular groove part 22n, it has a spring property in the radial direction.

Moreover, an annular collar part 22q outwardly projecting is provided at the rear end part of the annular projection part 22p of the core member 22, and an annular groove part 22r for mounting on a front end cylindrical part 60b of the main body cylinder 60 is formed on an outer peripheral face of the annular collar part 22q. Furthermore, an annular projection part 22s for mounting an application member press 28 to be mentioned below is formed on an outer peripheral face of the annular projection part 22p.

Furthermore, the core member 22 has a front end face curved in a umbrella-like shape and, as shown in FIG. 13 to FIG. 15, has a recessed part 22t with a circular cross section recessed from the front end face at an approximately center of the front end face. A projection part 22f frontwardly projecting is provided at the approximately center of the recessed part 22t. The projection part 22f is for controlling the flow of the washing liquid, and constituted to have a tapered conic-shape, and have a smaller outer diameter than that of the hole part 22a, and the front end of the projection part 22f frontwardly projects from a most front end position of the core member 22.

Furthermore, communication holes 22j communicating with the recessed part 22t and the hole part 22a are provided respectively at a position separated by every 120° in a peripheral direction on an outer peripheral position of the projection part 22f of the core member 22. The communication hole 22j has an approximately rectangular cross sectional-shape, and has a larger outer diameter than that of the hole part 22a.

The application member 23 is curved in an umbrella-shape so as to coincide with the front end face of the core member 22, as shown in FIG. 11 and FIG. 13, and has an annular projection part 23p at an outer peripheral end of the curved part. The annular projection part 23p rearwardly projects continuously through a stepped face 23r, and has a larger diameter than that of the outer peripheral end of the curved part, as shown in FIG. 13. An annular groove part 23b and a stepped annular projection part 23c are respectively formed on an inner peripheral face of the annular projection part 23p, and engaged with the annular projection part 22b and the stepped annular groove part 22c of the core member 22.

The application member 23 has a delivery hole 23f at an approximately center position. This delivery hole 23f has a smaller diameter than those of the recessed part 22t, the communication hole 22j and the hole part 22a of the core member 22, and communicates with a front end face 23a and a back face. The delivery hole 23f is constituted to have a circular cross sectional-shape. An opening on the front end face 23a of the delivery hole 23f is a delivery port 23g, and a group of many projections 23b are provided around the delivery port 23g, as shown in FIG. 11 and FIG. 13.

Furthermore, in this embodiment, the application member press 28 for pressing the application member 23 is provided, as shown in FIG. 12 and FIG. 13. As shown in FIG. 13, the application member press 28 is constituted to have a stepped cylindrical-shape. A small diameter part of the application member press 28 is continuous to a front end part of a large diameter part of the application member press 28 through a stepped face 28a, and the most of small diameter part can be inserted between the end cylindrical part 60b of the main body cylinder 60 and the annular projection part 22p of the core member 22. The application member press 28 has an annular collar part 28b inwardly projecting at the front end, and has an annular groove part 28s at a position close to a rear end of the inner peripheral face, and the annular projection part 22s of the core member 22 is fitted in the annular groove part 28s.

Moreover, the application member press 28, the application member 23 and the core member 22 are assembled as an assembly unit, and are mounted on the main body cylinder 60 after filling the washing liquid in the filling region 60a.

That is, the application member 23 is mounted on the core member 22 in the state that the back face of the application member 23 is closely contacted with the curved face at the front end of the core member 22, by externally putting the rear end side of the application member 23 so as to cover the front end side of the core member 22, and respectively engaging the annular groove part 23b with the annular projection part 22b of the core member 22 and the stepped annular projection part 23c with the stepped annular groove part 22c of the core member 22. The application member press 28 is mounted on the core member 22 in the state that the application member press 28 presses the application member 23, by externally putting a rear end side of the application member press 28 from the front end side of the core member 22, butting a rear end face of the application member press 28 against the annular collar part 22q of the core member 22, engaging an annular groove part 28s with the annular projection part 22s of the core member 22, and butting the annular collar part 28b against the stepped face 23r of the application member 23. Thereby, the assembly unit having the application member 23, the core member 22 and the application member press 28 is constituted. This assembly unit is mounted on the main body cylinder 60, by inserting the assembly unit from the front end side of the front end cylindrical part 60b of the main body cylinder 60, butting the stepped face 28a of the application member press 28 against the front end face of the front end cylindrical part 60b, and engaging the annular groove part 22r of the core member 22 with the annular projection part 60c of the front end cylindrical part 60b. At this time, the annular collar part 22q of the core member 22 is airtightly jointed to the inner peripheral face of the main body cylinder 60 due to the spring property thereof.

In this state, the hole part 22a of the core member 22 communicates with the filling region 60a.

Moreover, in this state, the predetermined inside space 24 is formed between the recessed part 22t of the core member 22 and the application member 23. With this inside space 24, the hole part 22a of the core member 22 communicates through the communication hole 22j, and an opening 23k at the side of the inside space 24 of the delivery hole 23f of the application member 23 communicates.

Furthermore, in this state, the projection part 22f of the core member 22 projects toward the delivery hole 23f of the application member 23, the front end part of the projection part 22f enters into the delivery hole 23f, and the outer face of the front end part is closed to the delivery hole 23f with the predetermined space.

In the applicator 21 constituted in this way, when the washing liquid is extruded from the filling region 60a according to the operation by a user, the washing liquid flows in the passage, which extends toward the delivery hole 23f of the application member 23 through the hole part 22a and the communication hole 22j of the core member 22 and the inside space 24. So, the washing liquid does not flow toward the delivery hole 23f straightly at once, but flows toward the delivery hole 23f in a roundabout way so that the resistance may be given to the flow, as shown with an arrow in FIG. 13. In addition, since the outer face of the projection part 22f of the core member 22 is closed to the delivery hole 23f, the delivery hole 23f is narrowed. Therefore, it can be prevented to deliver the washing liquid too much in application, the delivering amount becomes suitable, and thus the washing liquid is satisfactory applied.

At his time, since a group of many projections 23b having a brushing function is arranged around the delivery port 23g of the application member 23, the dirt of skin, especially, the dirt of pores can be effectively removed by a group of these projections 23b and the washing liquid.

Furthermore, even when an impact or a vibration by falling or the like, or a viscosity change or the like of the washing liquid by a temperature change is worked to the liquid cosmetic extrudable container 70 having such the applicator 21, since the delivery hole 23f is narrowed and the passage of the washing liquid is made roundabout, the leak of the washing liquid can be prevented. As the results, it can be prevented beforehand that a hand, clothing or the like becomes dirty.

In addition, the space between the outer face of the projection part 22f of the core member 22 and the delivery hole 23f can be adjusted depending on, for example, viscosity of the washing liquid or the like.

Furthermore, the communication hole 23j may be an inclined hole or the like. That is, it can be used, if the hole opens at the position except the front end of the projection part 22f of the core member 22, faces to the inside space 24, and communicates with the hole part 22a.

Further, although the outer diameter of the recessed part 22t of the core member 22 is large in this embodiment, since it is especially favorable, it can be also used, even if the outer diameter has the almost same diameter as that of the communication hole 22j, for example.

In addition, each of the above embodiments has the constitution, where the outer face of the projection part 2f (22f) is closed to the delivery hole 3f (23f) and has slight space, but it is possible to have other constitution, where the face of the projection part 2f (22f) contacts with the delivery hole 3f (23f) and closes the delivery hole 3f (23f). In such constitution, the same effects can be expected. That is, even when an impact or a vibration by falling the container or the like, or a viscosity change or the like of the washing liquid by a temperature change is worked, the leak of the washing liquid can be prevented. Further, when the washing liquid is extruded in application, the opening 3k (23k) at the side of the inside space 4 (24) of the delivery hole 3f (23f) of the application member 3 (23) is deformed so as to displace to the front end side since the application member 3 (23) is made of the soft elastic material. Therefore, stagnation of the washing liquid in application can be prevented, and the delivering amount becomes suitable, so that the washing liquid can be satisfactory applied through the delivery hole 3f (23f).

Furthermore, in each of the above embodiments, the projection part 2f (22f) of the core member 2 (22) is entered into the delivery hole 3f (23f) of the application member 3 (23), since it is especially effective to prevent the leak of the washing liquid. However, the projection part 2f (22f) may not be entered into the delivery hole 3f (23f).

Furthermore, in each of the above embodiments, the projection hole 3f (23f) of the application member 3 (23) has a circular shape (the delivery port 3g has an oval shape at this time), and the projection part 2f (22f) of the core member 2 (22) has the conic shape, because it is easy to manufacture and control the flow of the washing liquid. However, the delivery hole 3f (23f) may have an oval shape (the delivery port 3g has the circular shape at this time), or a rectangular shape, or the like, and the projection part 2f (22f) may have a pyramidal shape or the like, for example.

Furthermore, in each of the above embodiments, although the application member 3 (23) is mounted on the core member 2 (22), the application member 3 (23) can be directly mounted on the main body 10 (60) or the like, for example.

By the way, in each of the above embodiments, the washing liquid is used as an example of the liquid material filled therein, since it is especially suitable. However, it is not limited to the washing liquid, but the liquid material filled therein may also be a cosmetic solution, a nail care solution, a nail remover, a mascara, an anti ageing solution, a hair color, a cosmetic for hair, an oral care solution, a massage oil, a keratotic plug softening liquid, an ink of a writing tool such as a marking pen or the like, a liquefied medicine, a muddy material, a shoe polish, or the like.

Figure 16:
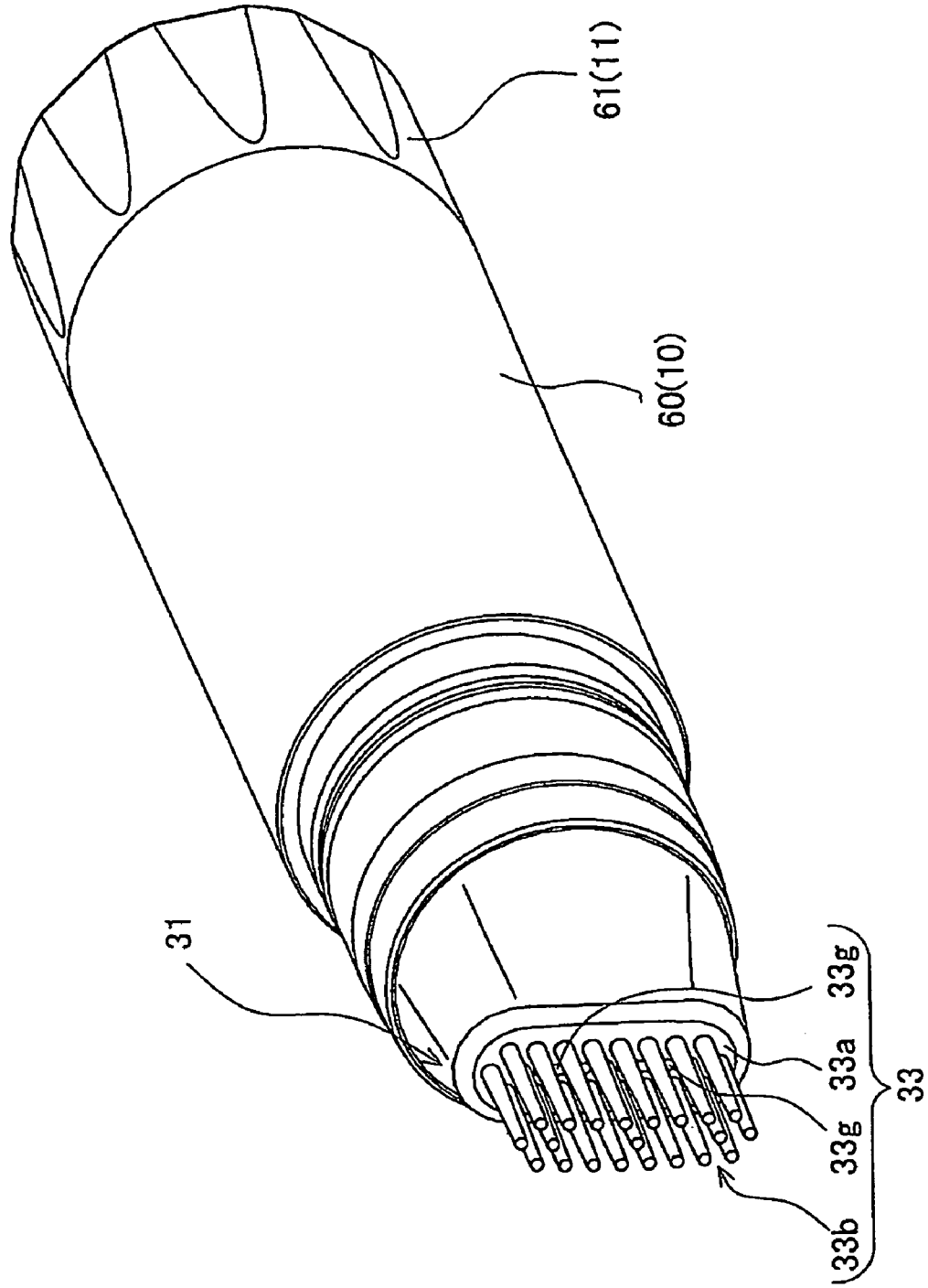
FIG. 16 is a perspective view showing another applicator applied to the liquid cosmetic extrudable containers in FIG. 1 and FIG. 12.
Figure 17:
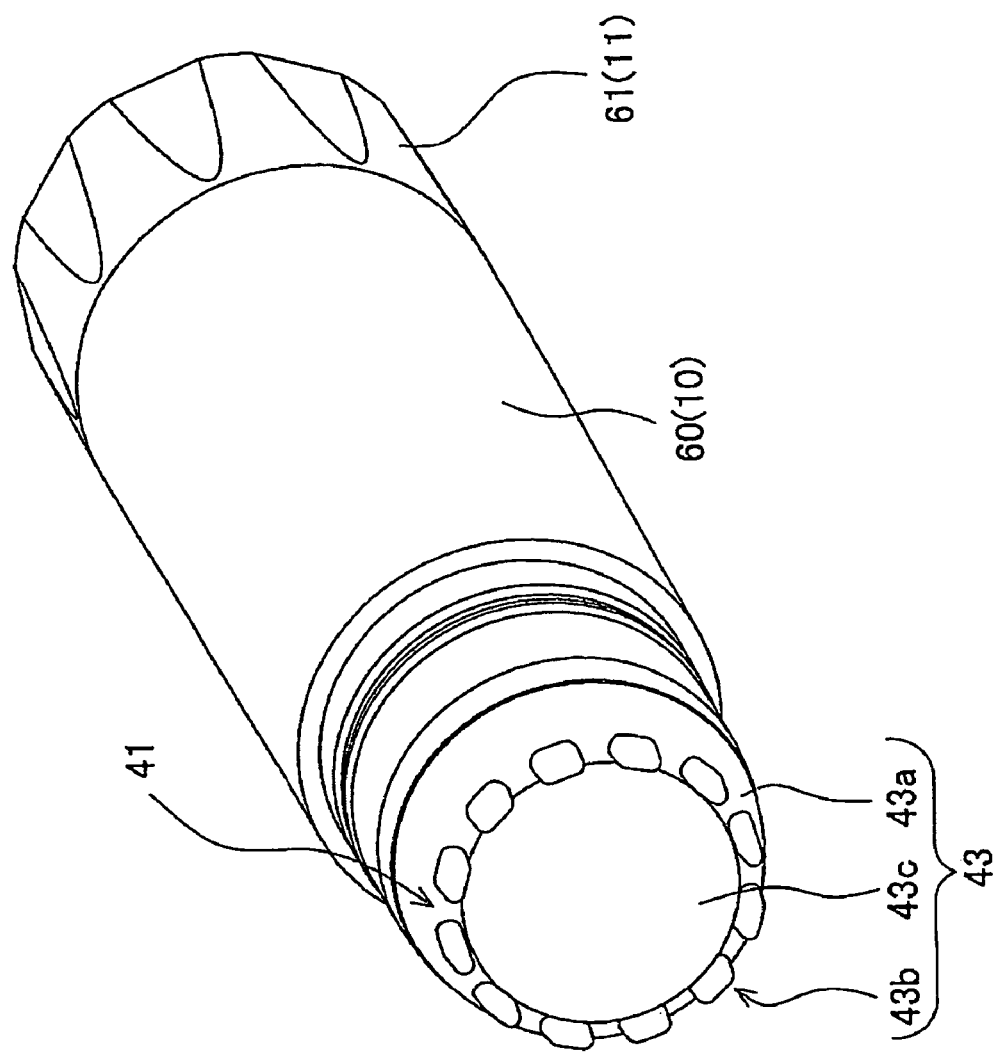
FIG. 17 is a perspective view showing another applicator applied to the liquid cosmetic extrudable containers in FIG. 1 and FIG. 12.
Figure 18:
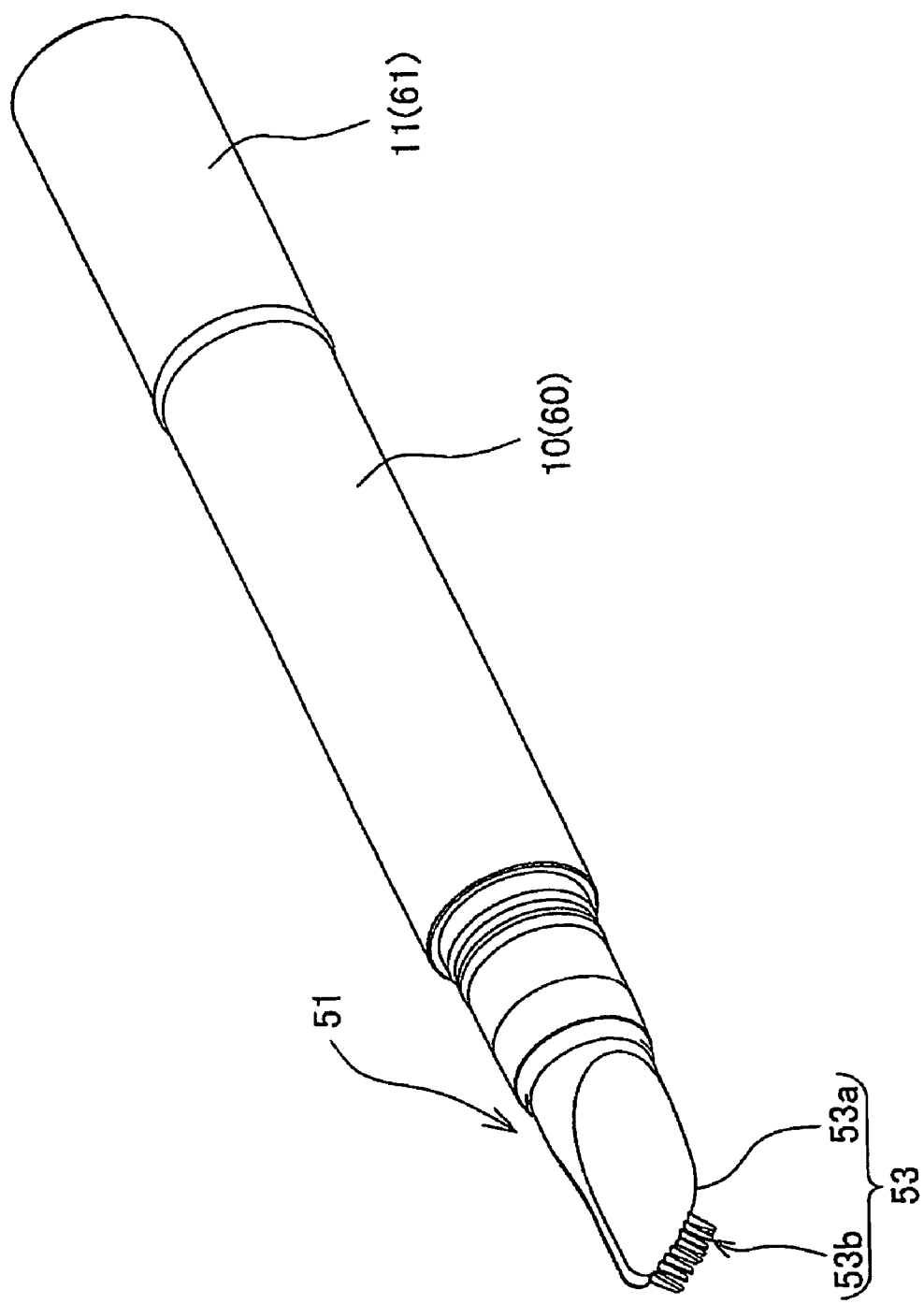
FIG. 18 is a perspective view showing another applicator applied to the liquid cosmetic extrudable containers in FIG. 1 and FIG. 12.

FIG. 16 to FIG. 18 are perspective views showing other applicators 31, 41, 51, which are applied to the liquid cosmetic extrudable containers of FIG. 1 and FIG. 12. The core members constituting these applicators 31, 41, 51 are the same as those of FIG. 1 and FIG. 12.

In the applicator 31 shown in FIG. 16, a front end face 33a of an application member 33 is constituted to have a vertical face with respect to the axis of the application member 33, and have a long ellipse shape as shown in the figure. Further, a delivery port 33g of the front end face 33a has an ellipse shape being similar to the shape of the front end face 33a and having the small diameter, and plural delivery ports 33g (two in the figure) are opened on the front end face 33a. Further, a group of projections 33b around these delivery ports 33g has a long pectinate shape.

Furthermore, in the applicator 41 shown in FIG. 17, a sponge-like application body 43c with a large diameter covering the delivery port is mounted on a front end face 43a of an application member 43, and a group of warty projections 43b are annularly arranged around the application body 43c.

Furthermore, in the applicator 51 shown in FIG. 18, an application member 53 is tapered toward a front end side so that a front end face 53a of the application member 53 has a narrow width. A group of projections 53b in a long pectinate shape is arranged in parallel to the longitudinal direction of the front end face 53a having a narrow width, and a group of the projections 53b are provided so as to position around a delivery port. A group of the projections 53b is provided so as to project in the direction inclined with respect to the axial direction of the application member 53.

Then, when such the applicators 31, 41, 51 having constitutions shown in FIG. 16 to FIG. 18 are suitably selected according to the above various liquid materials filled therein, the applicator can be used most suitably. By the way, when a group of the projections projects in the direction inclined with respect to the axial direction of the application member, as shown in FIG. 18, there is an advantage that functions of a group of the projections can be diversified.

Although the present invention is explained in the above based on the embodiments, the present invention is not limited to the above embodiments. For example, as for the extruding mechanism of the liquid material extrudable container used for extruding the above various liquid materials, it is not limited to the rotational type extruding mechanism mentioned above, but for example, a knock type extruding mechanism or the like may be used. Furthermore, the above various applicators 1, 21, 31, 41, 51 can be applied to a liquid material extrudable container of a simple squeeze type, such as a tube, a soft bottle or the like. When these applicators 1, 21, 31, 41, 51 are suitably selected according to various container types (an extruding type) and various liquid materials filled therein, the applicators can be used most suitably.

What is claimed is:

1. An applicator for containing a liquid filler and having a longitudinal axis, comprising:
    a container body defining a front section, and a filling region arranged so that a liquid filler filled in the body filling region can be extruded toward the container body front section;
    a core member defining a front section, and being connected to the container body front section, the core member defining a hole having an inlet and outlet, and extending along the applicator axis, the inlet of the core member hole communicating with the container body filling region;
    an application member formed of a soft elastic material, and defining front and rear sections, the application member including a recess formed at the rear section thereof, a delivery hole extending along the applicator axis and having an outlet and an inlet such that the inlet of the delivery hole communicates with the core member hole, and a delivery port located at the application member front section and in communication with the outlet of the delivery hole, the core member front section being inserted into the application member recess and directly connected therewith; and
    a tapered, conical-shaped projection element held by the outlet of the core member hole, the projection element having a front section disposed in the application member delivery hole inlet;
    wherein an inside space is defined between the core member front section and the inlet of the application member delivery hole, the inside space including roundabout passages permitting a liquid filler to move in a direction away from the longitudinal axis and through passages formed between the projection element and the application member that permit a liquid filler to move in a direction approaching the applicator axis.

2. The applicator as claimed in claim 1, wherein the application member has a projection line on a plurality of places in a circumferential direction of a circumferential face of the recess, the projection line extends from a bottom face side to the rear section of the application member and inwardly projects, the core member has a large diameter part and a first groove part, the large diameter part is defined between the rear and front from sections of the core member, the first groove part extends a predetermined length from the front section of the core member into the large diameter part, a second groove part is formed at a front end part of the first groove part so as to be recessed at a further inside of a front end part of the first groove part and to extend to a portion of the large diameter part, and a communication hole opening at the second groove part by overlapping an inside face of the second groove part and an outer circumferential face of the core member hole.

3. The applicator as claimed in claim 1, further comprising a group of projections having a brushing function arranged around the delivery port of the application member.

4. The applicator as claimed in claim 3, wherein the group of projections is constituted to project in the direction inclined with respect to an axial direction of the application member.

* * * * *